United States Patent [19]

Jewell et al.

[11] Patent Number: 5,147,287
[45] Date of Patent: Sep. 15, 1992

[54] NECK SUPPORT MEANS FOR CERVICAL SURGERY

[75] Inventors: Brian Jewell, Batavia, Ohio; Stephen M. Papadopoulos, Ann Arbor, Mich.

[73] Assignee: Ohio Medical Instrument Company, Cincinnati, Ohio

[21] Appl. No.: 671,012

[22] Filed: Mar. 18, 1991

[51] Int. Cl.$^5$ ............... A61F 5/00; A61G 13/00
[52] U.S. Cl. .................................. 602/32; 606/242; 602/33; 5/636
[58] Field of Search .............. 128/70, 71, 72, 73, 128/74, 75; 269/324, 322, 328; 297/403; 602/32, 33; 606/237, 238, 241, 242

[56] References Cited

U.S. PATENT DOCUMENTS

| | | |
|---|---|---|
| 1,529,872 | 1/1922 | Craig . |
| 3,572,835 | 3/1971 | Kees, Jr. et al. .............. 297/410 |
| 3,638,646 | 2/1972 | Draux . |
| 4,638,793 | 1/1987 | Therkorn . |
| 4,819,622 | 4/1989 | Taylor et al. . |
| 4,866,796 | 9/1989 | Robinson et al. . |

OTHER PUBLICATIONS

Ohio Medical Instrument Co brochure "Mayfield Neurosurgical Equipment".

Primary Examiner—Richard J. Apley
Assistant Examiner—Linda C. M. Dvorak
Attorney, Agent, or Firm—Wood, Herron & Evans

[57] ABSTRACT

For cervical surgery, the neck of the patient is lifted and arched slightly upwardly with the head being supported beyond the end of an operating table. The anterior spacing between the vertebrae of the patient's cervical spine is increased, thereby affording better surgical access.

12 Claims, 2 Drawing Sheets

NECK SUPPORT MEANS FOR CERVICAL SURGERY

FIELD OF THE INVENTION

This invention relates to means for supporting the head and neck of a supine patient for cervical surgery.

BACKGROUND

The cervical spine is that portion of the spine which is between the skull and the thorax. Surgery on the cervical spine is often performed with the patient in supine position, that is, lying on his back, face upward. Although the cervical spine lies closer to the back of the neck than the front, an injured or diseased area on the anterior side of the spine is usually better accessed by incision from the anterior side rather than from the posterior side. The windpipe, esophagus and other neck tissue are held aside laterally to expose the affected area.

In such surgery, the shoulders of the patient are usually positioned and secured right at the end of the operating table, with the head projecting beyond (off) the end of the table and supported by a head support. The surgeon is thereby enabled to more closely and more easily approach the site of the incision in the neck because the sides and end of the table do not interfere as much. Indeed, for a long operation the surgeon can sit directly beside the patient's neck.

Various types of head supports for supporting a patient's head off the end of an operating table for such surgery, are known in the art. The head support is generally not integral with the table but rather is removable and is cantilevered or attached to the table when needed. An operating table conventionally has one or more sockets at its head end to receive one or two support arms by which the head support is mounted to the table. The head support projects outwardly and upwardly from the table and may be adjustable in various directions to accommodate various socket spacings, distances from the table, head elevations, and so on. One example of such head support is shown in Kees et al U.S. Pat. No. 3,572,835, titled "Surgical Head Rest", issued Mar. 30, 1971.

Heretofore, when surgery on the cervical spine has been performed with the head of the patient supported beyond the end of the table, the neck has not been directly supported; traction, applied to the head with the patient's thorax secured by straps or tape to the operating table, holds the neck "suspended." However, although thus suspended, the neck tends to "sag" slightly between the end of the table and the head.

BRIEF DESCRIPTION OF THE INVENTION

It is believed that such downward sag of the cervical spine tends to undesirably reduce or close the spacing between the upper (anterior) sides of the vertebrae. If the vertebrae are likened to disks strung on a cord held in suspension, sag of the cord will angulate the disks (vertebrae) so that they are closer together on their upper sides than on their lower sides. Such closing makes anterior access to the cervical spine more difficult. It is now believed desirable to slightly lift the neck so as to "spread" the cervical vertebrae on the anterior side. In doing so, however, the neck must be lifted in a way which does not restrict the surgeon's access to the site of the operation, or prevent him from standing or sitting close beside the neck. An overhead support would restrict access from above; and a floor support would resist the ability to sit with knees beneath the neck.

In accordance with this invention a neck support is provided which holds the back of the neck upwardly from below so that the neck is arched slightly upward from the position it would occupy without such support. It has been found that a slight upward sagittal displacement of the cervical spine, of the order of about 1 to 2 inches upwardly from its position if only a head support were used, substantially improves access to the anterior side of the vertebrae. The slightly convex arch increases the anterior spacing between the vertebrae; moreover, stability and immobility for surgery are substantially improved.

In preferred form the neck support is mounted to and used with a head support. The head support, which may itself be conventional, has one or two parallel arms which are mountable to the head end of the operating table; the neck support is attachable to project upwardly from those arms, between the end of the table and the position at which the head support engages the head. It comprises at least one upright mounted to an arm of the head support, and a crosswise horizontal base which engages and lifts the back of the patient's neck. The head support usually has two parallel arms, and the neck support preferably has two uprights which are mounted to the respective arms of the head support. The base is preferably mounted horizontally to the upper ends across the uprights.

In the method of the invention the patient is placed supine on an operating table with his head and neck extending beyond the end of the table. The head is supported and traction may be applied to the head so that the vertebrae in the neck are placed in tension. The neck is lifted upward from below, at a position beyond the end of the table, sufficiently to arch it upwardly from the position it would occupy without such lifting and to open the spacing of the cervical vertebrae on the anterior side. Lifting the neck from below also provides better patient stability for the surgery.

DESCRIPTION OF THE DRAWINGS

The invention can best be further described by reference to the accompanying drawings, in which.

DETAILED DESCRIPTION

Figure 1:
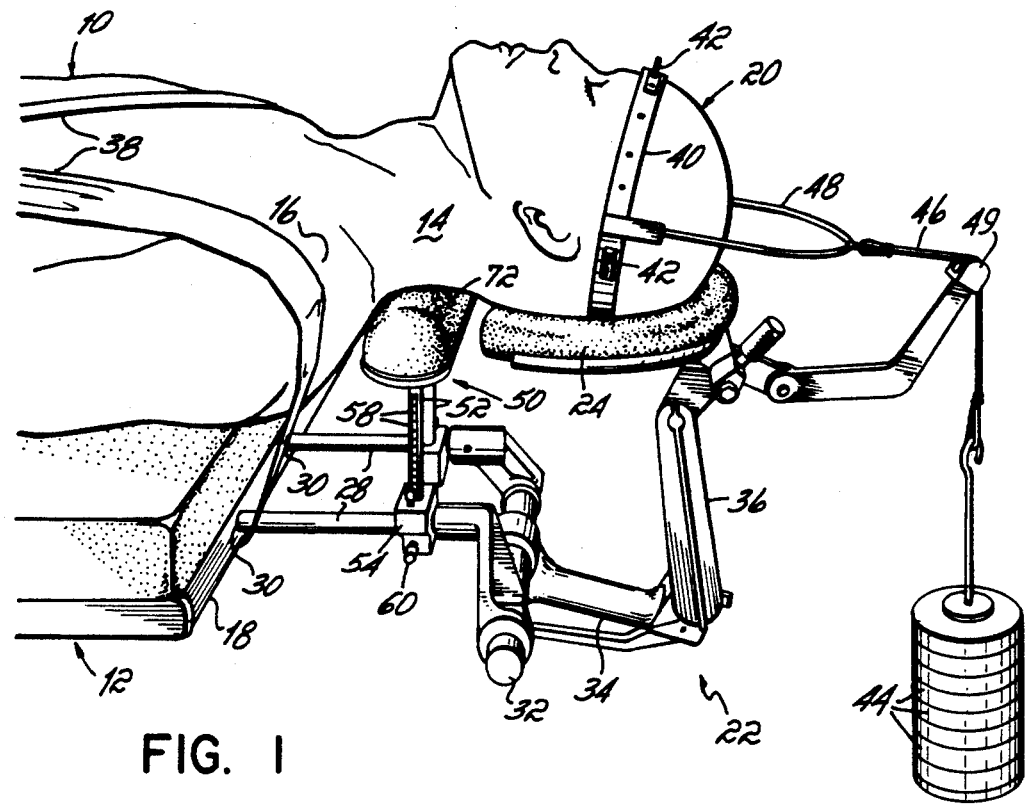
FIG. 1 is a perspective view of the thorax, neck and head of a patient supported for cervical surgery by apparatus in accordance with a preferred embodiment of the method and apparatus of this invention.

In FIG. 1 of the drawings a patient 10 is shown in supine position on an operating table 12 for an operation on the cervical spine in the neck area 14. As shown, the patient's body rests on table 12 with his shoulders 16 just at or slightly overhanging the head end 18 of the table. The patient's head 20 is supported off the end of the table by support means 22. The head support 22 lifts and cradles the patient's head from below, as by a horseshoe shaped cushion or collar 24.

More particularly, the head support apparatus 22 includes one, and preferably two, support arms 28, 28 in the form of rods which are mountable to the table as, for example, in corresponding sockets 30, 30 which are provided at the head end 18 of the table 12. The parallel, horizontal support arms are connected at their outer ends by a crossbar 32, to which an adjustable swing arm 34 and standard 36 are mounted. Cushion 24 is mounted to the upstanding end of standard 36. The head support, comprising elements 28, 30, 32, 34, and 36, may be similar to that further described in Kees U.S. Pat. No. 3,572,835, previously identified. Such devices are available commercially under the name and mark "MAY-FIELD."

Figure 3:
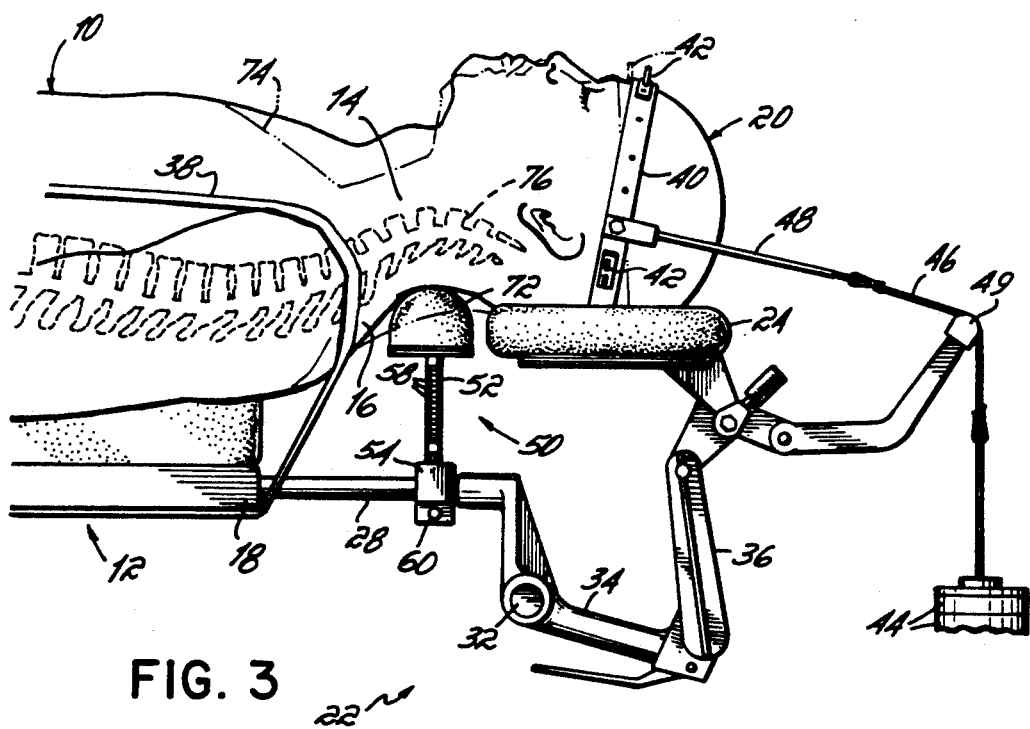
FIG. 3 is a side elevation of the patient and apparatus of FIG. 1, showing in solid lines the uplifted position of the neck in comparison to the position the neck would occupy without the neck support (shown in phantom lines).

As shown in side elevation in FIG. 3, the head cushion 24 holds the patient's head 20 slightly elevated with respect to the plane of the top of the operating table. The skull may be usually drawn in traction away from the patient's thorax, which is immobilized as by tape 38 to the table 12. In the embodiment shown a skull ring 40 is rigidly secured by pins 42 to the skull of the patient, and a tensioning weight 44 is connected by a line 46 to a bail 48 connected to skull ring 40. Line 46 extends over a pulley 49 mounted by a bracket projecting from support standard 36. This arrangement places the cervical spine in tension and thus tends to increase the spacing between the vertebrae of the cervical spine, see FIG. 3.

In the past, for operations on the cervical spine the patient's neck was not directly supported but rather was held in traction as by a skull ring 40, the patient's body being secured to the table by tape or straps.

In accordance with this invention, a neck support generally designated by 50 is provided which lifts the patient's neck above the position it would otherwise occupy between the head support and the table, as shown in FIG. 3. More specifically, neck support 50 includes two uprights 52, 52, which are mountable to the respective support arms 28, 28 of the head support, as by mounting brackets 54, 54. Each bracket 54 has a horizontal bore through which the respective support arm 28 extends. The bracket is slidable along the arm and can be fixed in position as by a screw 56. The uprights 52 are received in vertical bores in the brackets 54. Preferably ratchet means are provided whereby each upright 52 can be moved upward but not downward relative to the mounting brackets 54, in small increments. The ratchet means preferably includes a series of ratchet teeth 58 extending along the upright, which are engaged by a spring-loaded detent 60 in bracket 54. By pulling it outwardly, detent 60 can be disengaged from the ratchet teeth 58 so that the neck support can be lowered.

Figure 2:
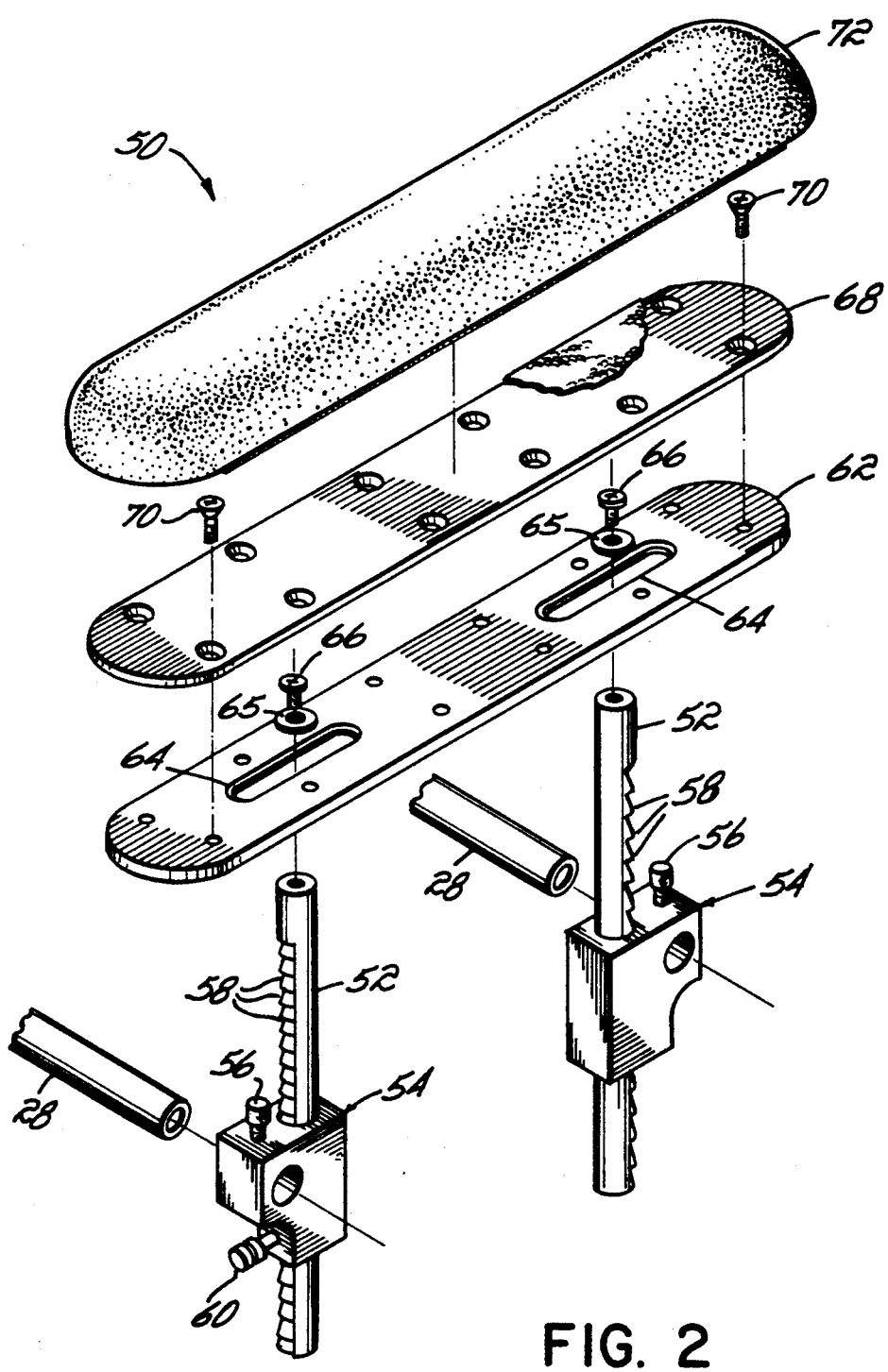
FIG. 2 is an exploded perspective of the apparatus of FIG. 1.

A neck support base 62 in the form of an elongated plate, for example about 7½ inches long (direction transverse to the arms)×2 inches wide, is mounted across the two uprights 52, 52 and preferably is secured to them at their upper ends. More specifically, as shown in FIG. 2, base 62 has a pair of shouldered longitudinal slots 64, 64. The shoulder in each slot 64 carries a washer 65 which is slidable along the slot, the washer being secured to the upper end of the respective upright 52 by a screw 66. The uprights are thus shiftable to accommodate different spacings between the table sockets 30, 30. The heads of screws 66, 66 are preferably recessed in the washers, within the thickness of base 62, so that they do not project above it. Base 62 is covered by an overlaying top plate 68, which may have a similar outline shape and which covers the slots 64 and screws 66 of the base. Recessed screws 70 secure top plate 68 to base 62.

A neck cushion 72 is mounted on top of top plate 68, and preferably slightly overhangs the top plate. Preferably the cushion is of surgical foam material and is secured to plate 68 by strips of hook and eye material, e.g., VELCRO brand material.

In the use of the invention, the support arms 28 of head support 22 are mounted in accordance with conventional practice. The neck support is mounted on the support arms, and the neck support uprights are slid on the base plate to fit the spacing of support arms 28, 28. The patient 10 is placed on table 12, and the head cushion is positioned in the usual manner. Base 64 is pulled upwardly until the cushion engages the back of the neck and lifts the neck upwardly by about 1 to 2 inches from the position at which the cushion first engages the neck.

The effect of lifting the neck is shown diagrammatically in FIG. 3, wherein the dashed or phantom line 74 shows the approximate position of the neck if the head support is used without the neck support. The neck support lifts the neck to the position shown by the solid lines. Lifting has the effect of relatively increasing the spacing on the anterior (upper) side of the cervical vertebrae 76, thereby facilitating surgical access. Moreover, the support holds the neck more securely for the surgery.

Having described the invention, what is claimed is:

1. In combination, a surgical operating table having a head support for supporting a patient's head beyond an end of the table, said head support having two arms mounting it to an end of the table, and a neck support for supporting the neck of a patient for cervical surgery while the head is supported on said head support,
    said neck support being mountable to said head support between said end of said table and said head support and comprising,
        two uprights mountable to the respective arms of said head support,
        a base mounted transversely to said upright,
        each said upright being laterally movable relative to said base, whereby said base can accommodate different spacings between said uprights, and
        a cushion mounted to said base, said cushion shaped to engage the back of a patient's neck and lift the neck upwardly from the position the neck would occupy without the neck support, such lifting thereby relatively increasing the anterior spacing between the vertebrae of the patient's cervical spine,
    said base having slots transverse to said arms and being adjustably connected to said uprights by fastening means which extend through said slots.

2. The combination of claim 1 further including a top plate facially engaging said base, said top plate covering said slots and mounting said cushion.

3. The combination of claim 1 wherein said base extends across said two uprights of said neck support.

4. The combination of claim 3 wherein said base is mounted horizontally across upper ends of said two uprights.

5. The combination of claim 1 wherein said uprights are vertically movable relative to said arms.

6. The combination of claim 5 further including ratchet means whereby said uprights can be shifted upwardly in increments and which restrain downward movement of the uprights.

7. The combination of claim 5 wherein said base is vertically movable relative to said head support.

8. The combination of claim 1 wherein said base extends transversely to said support arms.

9. The combination of claim 1 wherein said cushion is relatively narrow and elongated and is positioned in use to extend transversely beneath the neck of a patient.

10. The combination of claim 9 further including hook and pile attachment means which removably attach said cushion to said neck support.

11. In a surgical procedure for operating on the cervical vertebrae from the anterior side, wherein the patient is placed supine on a surgical operating table with the head and neck extending beyond a head end of the table, the patient's head is supported off the end of the table, and traction is applied to the patient's head with the thorax secured to the table, the improvement comprising, applying the upward lifting force to the back of the neck at a position beyond the end of the table, to lift and support the neck by a sagittal distance of about 1 to 2 inches above the position it would occupy without said lifting force, thereby holding the neck arched upwardly and opening the cervical vertebrae on the anterior side, whereby better surgical access is provided.

12. The improvement of claim 11 further wherein the head is supported by a head support which is cantilevered from a table, and said neck is supported by pushing upwardly from a portion of a head support between said table and the head.

* * * * *